United States Patent [19]

Hosokawa

[11] Patent Number: 4,824,652
[45] Date of Patent: Apr. 25, 1989

[54] METHOD FOR TREATING ACTIVATED SILICON POWDER

[75] Inventor: Hidehiko Hosokawa, Chiba, Japan

[73] Assignee: Toray Silicone Company, Ltd., Tokyo, Japan

[21] Appl. No.: 27,576

[22] Filed: Mar. 18, 1987

Related U.S. Application Data

[63] Continuation of Ser. No. 844,928, Mar. 27, 1986, abandoned.

[30] Foreign Application Priority Data

Apr. 9, 1985 [JP] Japan .................................. 60-75140

[51] Int. Cl.$^4$ ...................... C01B 33/02; C01B 33/08; C01B 33/00
[52] U.S. Cl. .................................. 423/348; 423/324; 423/342; 423/343
[58] Field of Search ............... 423/342, 335, 348, 324, 423/343

[56] References Cited

U.S. PATENT DOCUMENTS 3,353,997  11/1967  Walaschewski ...................... 134/22

FOREIGN PATENT DOCUMENTS

| 0201199 | 11/1986 | European Pat. Off. ............ 423/348 |
| 2362494 | 12/1976 | Fed. Rep. of Germany . |
| 3131732A1 | 2/1983 | Fed. Rep. of Germany . |
| 3523541 | 1/1987 | Fed. Rep. of Germany . |

OTHER PUBLICATIONS

Perry et al, Chemical Engineers' Handbook, 5th edition, 1973, pp. 8-59.
Mellor, A Comprehensive Treatise on Inorganic and Theoretical Chemistry, vol. VI, 1949, pp. 160-161.

*Primary Examiner*—John Doll
*Assistant Examiner*—Lori S. Freeman
*Attorney, Agent, or Firm*—Carl A. Yorimoto

[57] ABSTRACT

What is disclosed is a method for treating a reaction residue from the preparation of organochlorosilanes or chlorosilanes from the reaction of metallic silicon with a chlorinated hydrocarbon or hydrogen chloride, said method comprising (A) combining the reaction residue with water, and (B) granulating the mixture of water and silicon from (A).

2 Claims, No Drawings

METHOD FOR TREATING ACTIVATED SILICON POWDER

This is a continuation of co-pending application Ser. No. 844,928 filed on Mar. 27, 1986 now abandoned.

BACKGROUND OF THE INVENTION

This invention relates to a method for treating the reactive silicon powder obtained as a reaction residue of the reaction of metallic silicon and a chlorinated hydrocarbon to prepare organochlorosilanes or the reaction of metallic silicon and hydrogen chloride to prepare chlorosilanes.

The reaction of metallic silicon and a chlorinated hydrocarbon to prepare organochlorosilanes and the reaction of metallic silicon and hydrogen chloride to prepare chlorosilanes is widely practiced on a commercial-scale. The reaction of metallic silicon with a chlorinated hydrocarbon can be such reactions as (1) the preparation of methylchlorosilanes such as methyltrichlorosilane, dimethyldichlorosilane, trimethylchlorosilane, or methyldichlorosilane from the reaction of metallic silicon and methyl chloride; (2) the preparation of phenylchlorosilanes such as phenyltrichlorosilane, diphenyldichlorosilane, or phenyldichlorosilane from the reaction of metallic silicon and chlorobenzene; (3) the preparation of ethylchlorosilanes from metallic silicon and ethyl chloride. The reaction of metallic silicon and hydrogen chloride produces chlorosilanes such as tetrachlorosilane and trichlorosilane.

Various methods are practiced in carrying out the reactions, supra. Generally, the metallic silicon is finely divided and is reacted with the chlorinated hydrocarbon or hydrogen chloride in a fluidized bed. A catalyst such as copper is generally added to the reaction. However, regardless of the specific method of carrying out the reactions, supra, and distillation of the produced organochlorosilanes or chlororsilanes not all of the metallic silicon will react and a portion of the starting metallic silicon will finally remain as a residue from the reaction. The portion of the starting metallic silicon that will remain as a residue will depend upon the particular starting materials, the purpose of the run, and the operating conditions.

The metallic silicon residue poses a safety hazard, since it is still chemically reactive. This powdered reaction residue readily undergoes spontaneous combustion upon contact with the atmosphere and reacts with water to produce hydrogen. The particle size of this powdered, reactive silicon reaction residue will vary, but generally the particle size is in the range of 1 to 200 microns. The silicon powder, being a powder, is difficult to handle for purposes of moving to waste disposal or to means of reuse. Before the instant invention, no method has been disclosed for treating the reactive silicon powder to reduce the powder's reactivity and to improve its handling.

The objective of the instant invention is to provide ease of handling and to reduce the reactivity of the silicon powder, obtained as a reaction residue from the preparation of organochlorosilanes or chlorosilanes from metallic silicon and a chlorinated hydrocarbon or hydrogen chloride, to a practical level of safe operation.

The instant invention achieves this objective, supra, by the method of combining the reactive silicon powder reaction residue, obtained from the preparation of organochlorosilanes or chlorosilanes from metallic silicon and a chlorinated hydrocarbon or hydrogen chloride, with water and then granulating the silicon powder.

DESCRIPTION OF THE INVENTION

In accordance with the instant invention there is provided a method to reduce the reactivity of the silicon powder, obtained as a residue from the preparation of organochlorosilanes or chlorosilanes from metallic silicon and a chlorinated hydrocarbon or hydrogen chloride, under conditions that will be delineated herein. What is described, therefore, is a method for treating reactive silicon powder, obtained as a reaction residue from the preparation of organochlorosilanes or chlorosilanes from the reaction of metallic silicon with a chlorinated hydrocarbon or hydrogen chloride, said method comprising (A) combining the reactive silicon powder with water, and (B) granulating the mixture of water and silicon from (A).

In order to combine the reactive silicon powder with water and then to granulate it, the reactive silicon powder is first placed in a granulating device and then combined with water, preferably with mixing. Preferred granulating devices are tumbling granulators and mixing granulators.

The quantity of water added to the reactive silicon powder will depend upon the reactivity and particle size of the reactive silicon powder. The quantity needed is generally in the range of 5 to 50 weight percent of the combined reactive silicon powder/water mixture. Preferably, the quantity of water in the combined silicon powder/water mixture is in the range of 15 to 40 weight percent. When too little water is added, the affinity between the reactive silicon powder and water will be inadequate to effect sufficient adhesion of powder particles to allow granulation to occur. When too much water is added, the mixture will form a paste or slurry and, again, granulation will not occur.

The reactive silicon powder should be mixed with water under an inert atmosphere, such as nitrogen or helium, to prevent combustion. In addition to water, inert organic powders such as calcium carbonate, slaked lime, magnesium oxide, talc, or clay may also be added.

The water undergoes an exothermic reaction with the reactive silicon powder. It is thought that the water oxidizes the reactive silicon powder to silicon dioxide. The reactive silicon powder is deactivated by conversion to silicon dioxide. Furthermore, the water functions as a binder in the granulation of the reactive silicon powder and accelerates granulation. Also, the heat generated by the reaction of water with the reactive silicon powder will dry the granules, thus having the effect of physically strengthening the resultant granules.

In the method of the instant invention reactive silicon powder, obtained as a reaction residue from the reaction of metallic silicon with a chlorinated hydrocarbon or hydrogen chloride to prepare organochlorosilanes or chlorosilanes, is combined with water and then granulated. As a result, the reactivity of the reactive silicon powder is rapidly reduced to a level safe for practical applications. The binder activity of the water accelerates granulation. The heat of reaction of the reactive silicon powder with water accelerates drying of the particles, with the result that particles of high physical strength are obtained. Due to these results, easier handling and transportation of the powder for waste disposal or for other uses is facilitated.

The following examples are presented to be illustrative of the instant invention and are not to be construed as limiting the instant invention delineated in the claims.

EXAMPLE 1

Reactive silicon powder, obtained as a residue from the reaction of metallic silicon powder and methyl chloride to produce methylchlorosilanes, was granulated in a tumbling granulator. The pan of the tumbling granulator had a diameter of 1000 millimeters.

First, 3.0 kilograms of reactive silicon powder was placed in the pan of the granulator. Water was then gradually and continuously added, with the pan rotating at 20 revolutions per minute at a pan angle of 45°. Heat was generated by the reaction of the reactive silicon powder with water. A nitrogen gas flow was established in the granulator and continued throughout the run. A total of 1.0 kilogram of water was added to the granulator over a period of 1 minute.

The granulation operation yielded spherical particles with particle sizes in the range of 2 to 50 millimeters in diameter. The ignition point in air of the reactive silicon powder before granulation was approximately 100° C. The ignition point in air of the particles immediately after granulation was approximately 220° C. The granulated particles did not adhere to each other. Further, when the granulated particles were dropped from a height of 2 meters onto a concrete floor, the granulated particles did not fracture. The principal components of the granulated particles are thought to be reactive silicon and silicon dioxide.

EXAMPLE 2

Granulation was carried out, as described in Example 1, on a reactive silicon powder obtained as a residue from the reaction of metallic silicon powder and hydrogen chloride to prepare chlorosilanes. The results were similar to those obtained in Example 1.

EXAMPLE 3

Granulation was carried out in a mixer granulator with a reactive silicon powder obtained as a residue from the reaction of metallic silicon with methyl chloride to prepare methylchlorosilanes. The inside diameter of the vat of the mixer granulator was 350 millimeters.

5.0 kilograms of the reactive silicon powder was placed in the vat of the granulator. Next, 1.3 kilograms of water was added under a nitrogen flow at a blade rotation in the vat of 200 revolutions per minute. Blade rotation was continued for 5 minutes after the completion of the addition of the water. The evolution of heat was observed during this time due to the reaction of the reactive silicon powder with the water.

The resultant granules were spherical particles with particle sizes ranging from 1 to 4 millimeter in diameter. The ignition point in air of the reactive silicon powder before granulation was approximately 100° C. The ignition point of the particles immediately after granulation was approximately 250° C. The particles did not adhere to one another. The granules were not fractured when dropped from a height of 2 meters onto a concrete floor. The principal components of the particles after granulation are thought to be reactive silicon and silicon dioxide.

EXAMPLE 4

Granulation was carried out in a mixer granulator with a reactive silicon powder that was obtained as a residue from the preparation of methylchlorosilanes from the reaction of metallic silicon powder and methyl chloride. The inside diameter of the vat of the mixer granulator was 1200 millimeters.

350 kilograms of reactive silicon powder and 20 kilograms of slaked lime were placed in the vat of the granulator. 85 kilograms of water was added to the granulator vat under a nitrogen gas flow at a blade rotation in the vat of 70 revolutions per minute. After the water addition, blade rotation was continued for 5 minutes. During this time heat was evolved due to the reaction of water and the reactive silicon powder.

The resultant particles were spherical and had a particle size in the range of 1 to 4 millimeters in diameter. The ignition point in air of the reactive silicon powder before granulation was approximately 100° C. The ignition point in air of the particles was approximately 250° C. immediately after granulation. The particles did not adhere to one another. The particles did not fracture, even when dropped 2 meters onto a concrete floor. The principal components of the particles are thought to be reactive silicon powder and silicon dioxide.

What is claimed is:

1. A method for treating reaction residue from the preparation of organochlorosilanes or chlorosilanes from the reaction of metallic silicon with chlorinated hydrocarbon or hydrogen chloride, said reaction residue being chemically reactive and readily undergoing spontaneous combustion upon contact with the atmosphere, said method comprising
    (A) combining the reaction residue with water, wherein the amount of water combined with the reaction residue is in a range from about 5–50 weight percent, based upon the weight of the reaction residue; and
    (B) granulating the mixture of water and reaction residue from (A), utilizing heat of reaction from reaction of the reaction residue with water to dry resulting granules and to physically strengthen the granules.

2. A method according to claim 1, wherein the amount of water combined with the reaction residue is in the range of 15–40 weight percent, based upon the weight of the reaction residue.

* * * * *